United States Patent [19]

Tkachuk

[11] Patent Number: 4,553,425
[45] Date of Patent: Nov. 19, 1985

[54] DYNAMIC PRESSURE TEST UNIT-RATIO METHOD

[75] Inventor: Peter R. Tkachuk, Exeter, N.H.

[73] Assignee: The United States of America as represented by the Secretary of the Navy, Washington, D.C.

[21] Appl. No.: 576,229

[22] Filed: Feb. 2, 1984

[51] Int. Cl.⁴ .................................. G01M 5/00
[52] U.S. Cl. ....................................... 73/37
[58] Field of Search ............................. 73/37, 149

[56] References Cited

U.S. PATENT DOCUMENTS

| | | | |
|---|---|---|---|
| 3,230,760 | 1/1966 | Fryer, Jr. et al. | 73/37 |
| 3,365,933 | 1/1968 | Jorgensen et al. | 73/37 |
| 3,555,881 | 1/1971 | Ayers | 73/37 |
| 3,613,436 | 10/1971 | Drake et al. | 73/37 |
| 3,916,673 | 11/1975 | Gass et al. | 73/37 |

Primary Examiner—Stewart J. Levy
Assistant Examiner—Joseph W. Roskos
Attorney, Agent, or Firm—Robert F. Beers; Arthur A. McGill; Prithvi C. Lall

[57] ABSTRACT

A dynamic pressure test unit is utilized to determine the yield point of a flask. For a period of time prior to the yield point being reached the ratio of the pressure vs. volume of water pumped into a test flask assumes a constant value. After reaching the yield point the volume indication increases at a faster rate than the pressure giving a negative slope to a line on a stripchart recorder that indicates the pressure divided by the volume of water pumped into the flask.

1 Claim, 3 Drawing Figures

DYNAMIC PRESSURE TEST UNIT-RATIO METHOD

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

A system for pressurizing a vessel with a non-compressible fluid and determining the pressure the vessel can withstand. In the present invention a flask is used as the vessel and a determination is made as to the internal pressure in the flask that corresponds to the yield point.

(2) Description of the Prior Art

There are a multitude of systems in use that determine the yield point of a flask. A large number of them correspond to the present invention in that water is used to form a variable pressure on the internal portion of the flask. The water pressure is increased and a determination is made as to the internal pressure of the water that causes deformation of the flask.

There are basically two methods of determining yield in a flask. The first method is called the volumetric expansion tank method, and the second method is called the dynamic pressure test unit method. The volumetric expansion tank method requires that the test be conducted on a fixed test bed in a controlled area, i.e., shop. It requires the use of a tank into which the test flask is placed. Both the tank and flask are filled with water. Additional water is then pumped into the flask to a predetermined level. If the flask should yield under the additional pressure, an amount of H₂O proportional to the expansion of the flask is measured in a Burrette attached to the test tank.

An improvement on the volumetric expansion tank method came with the dynamic pressure test unit. This method enables the test unit to be brought to the flask and eliminates the necessity for a test tank. The dynamic pressure test unit pumps water into the flask and records the proportional increase in pressure and volume on an x-y chart recorder. A yield in the flask is indicated by a non-linearity in the plot of pressure vs. volume on the recorder.

SUMMARY OF THE INVENTION

The present invention comprises a type of dynamic pressure test unit. A flask is filled with water and then additional water is pumped into the flask. The volume of water pumped and the internal pressure of the flask are measured. Prior to the yielding of the flask the increases in pressure and volume are proportional to each other. The present system provides a continuous strip chart recording of the pressure/volume. The quotient is a constant prior to the yield point being reached. Following the yield point a negative sloping curve is provided.

DESCRIPTION OF THE PREFERRED EMBODIMENT

Figure 1:
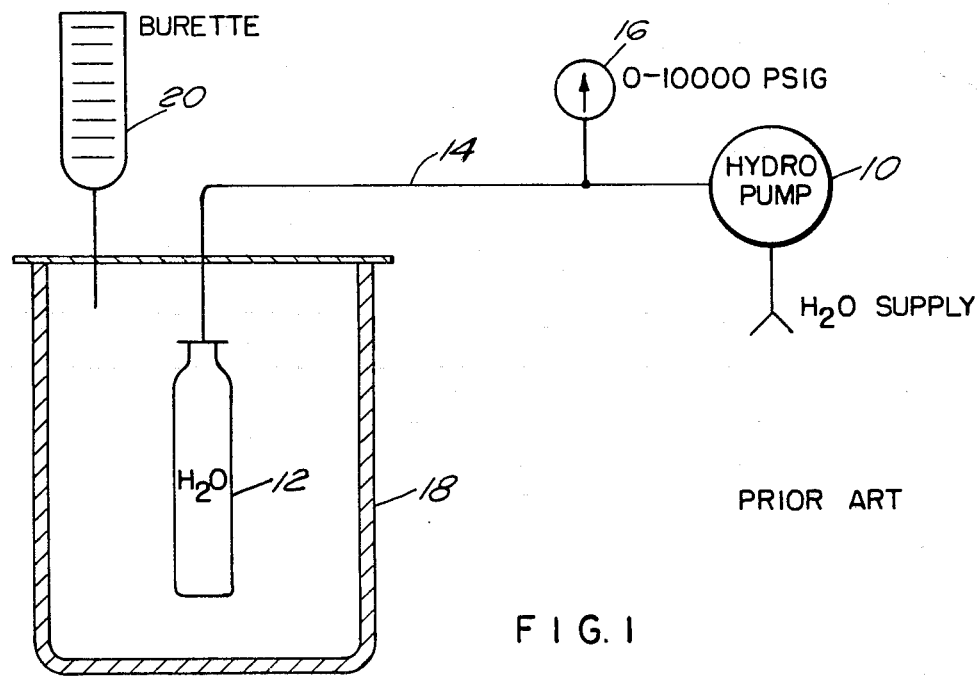
FIG. 1 is a diagrammatic representation of a typical prior art system showing the volumetric expansion tank method of determining the yield point in a flask.

Referring now to FIG. 1 there is shown a typical prior art volumetric expansion test setup. A hydro pump 10 is used to pressurize a flask 12 with water through a line 14 The line 14 has a pressure gage 16 for measuring the water pressure used in the test. The flask 12 is immersed in water in a test tank 18. As the pressurized flask 12 expands, the volume of the flask 12 forces water from the test tank 18 into a Burrette 20. The increased volume of the flask 12 is equal to the amount of water displaced into the Burrette 20. A manual plot of pressure vs. volume determines the integrity of the flask and provides a record of the test.

Figure 2:
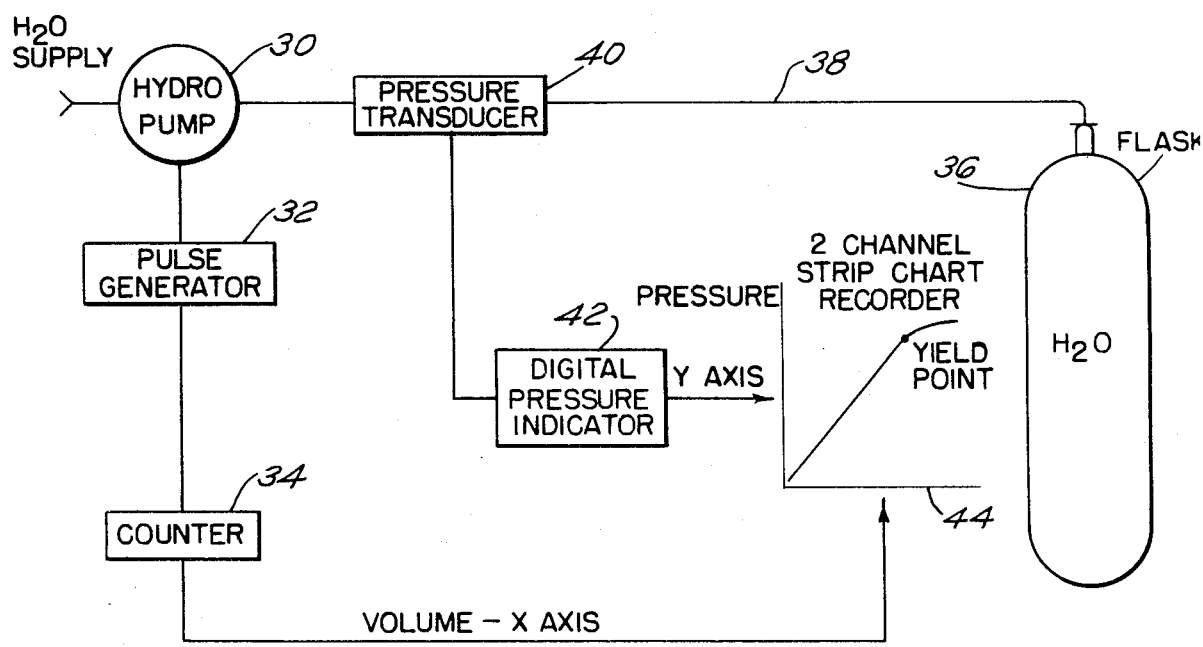
FIG. 2 is a diagrammatic representation of a typical prior art system showing the dynamic pressure test unit method of determining the yield point in a flask.

Referring now to FIG. 2 there is shown a typical prior art dynamic pressure test unit. A hydro pump 30 has connected to it a pulse generator 32 and a counter 34 for representing the calibrated volume of water pumped into a test flask 36. The water is pumped through a line 38 that has a pressure transducer 40 connected to a digital pressure indicator 42. A two channel strip chart recorder 44 has its x-axis connected to counter 34 for receiving a signal indicative of water volume and its y-axis connected to digital pressure indicator 42 for receiving a signal indicative of water pressure. A yield in the flask is indicated by a non-linearity in the plot of pressure vs. volume on the strip chart recorder 44.

Figure 3:
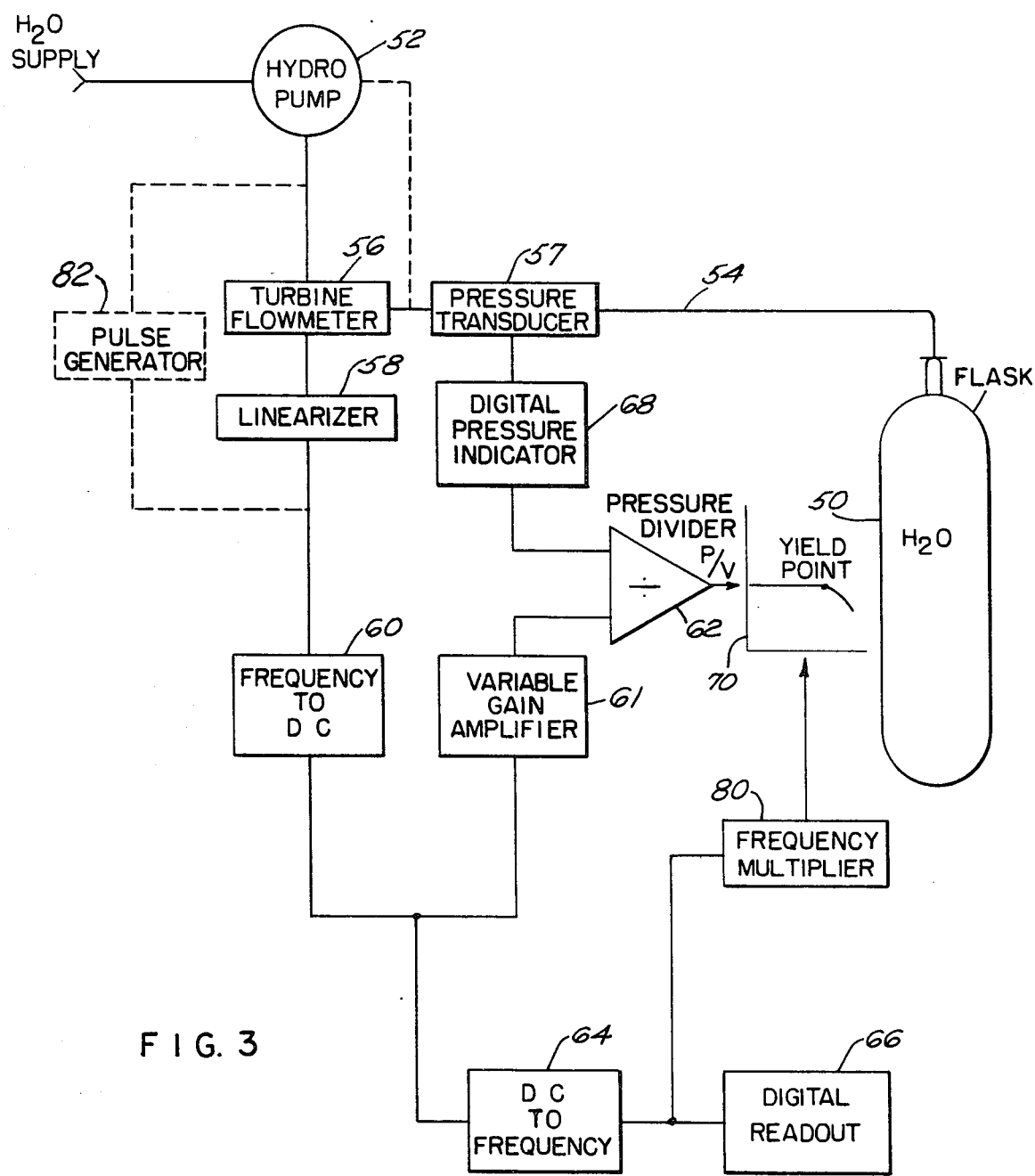
FIG. 3 is a diagrammatic representation of a system in accordance with the present invention.

FIG. 3 shows an embodiment of the present invention of a dynamic pressure test unit using a ratio method for determining the yield point of a flask 50. Water is supplied to the flask 50 by a hydro pump 52 through a line 54 that has a turbine flowmeter 56 and a pressure transducer 57.

The turbine flowmeter 56 is a typical state of the art device having a freely suspended axial turbine that is rotated by the flow of fluid through the flowmeter 56. The rotational speed of the turbine is proportional to the velocity of the fluid. Since the flow passage is fixed, the turbine's rotational speed is also a true representation of the rate of volume of fluid flowing through the flowmeter 56. The rate of volume can be expressed in various engineering units, i.e., GPM, LPM, CFM. The rotation of the turbine is sensed through the flowmeter body by an externally-mounted magnetic pickoff on the surface directly above the flowmeter rotor. The rotation of this turbine rotor produces a train of pulses in the pickoff. The frequency of these pulses is directly proportional to the volume flow rate. The pulses are then transmitted to an appropriate linearizer 58 near the flowmeter 56.

The linearizer 58 is a standard unit that minimizes the effects of magnetic drag and increases the range and linearity of the flowmeter 56. A pickoff coil located on the flowmeter 56 is an integral part of an oscillator ckt. The oscillator frequency is modulated by the turning rotor blades of the flowmeter 56 passing the pickoff. The linearizer conditions and converts this modulated carrier signal to a pulse output whose frequency is proportional to the rotation of the flowmeter rotor.

A frequency to DC transmitter 60 accepts the pulsed output of the linearizer 58 and provides a fully conditioned and amplified linear DC output proportional to the input frequency. This output feeds a variable gain amplifier 61 that in turn provides the volume input of the divider module 62. The DC transmitter 60 also provides the input of the DC to frequency converter 64.

The DC to frequency converter 64 provides an input frequency to a digital counter readout 66 that is proportional to the DC analog output from the frequency to DC transmitter 60. The digital counter readout 66 indicates volume from the total count of the turbine flowmeter 56.

In the pressure measuring portion of the system the pressure transducer 57 has a DC output proportional to the pressure induced by the hydro pump 52. The pressure transducer is a state of the art device that is made of stainless steel and is proof-tested to 1.5 times its maximum operating pressure. It has a built-in amplifier, zero adjust, input regulation, output short circuit protection and input reverse polarity protection. The output of the transducer 57 feeds a DC signal directly into a digital pressure indicator 68.

The digital pressure indicator 68 accepts the DC output of the pressure transducer 57 and indicates the pressure in the flask. A DC signal from the digital pressure indicator 68 equal to the output of the pressure transducer 57 is fed to the pressure input of the divider module 62.

The divider module 62 provides a DC output proportional to the quotient of the two DC inputs; one from the digital pressure indicator 68 representing pressure and the other from the frequency to DC transmitter 60 representing volume. As long as volume and pressure are proportional, due to no yield on the flask 50, the output of the divider module 62 will be some constant DC level. When the flask 50 yields, there will not be a corresponding increase in pressure per increase of volume of water pumped into flask 50. This causes the output of the divider module 62 to provide a decreasing signal that is plotted as a negative sloping curve by stripchart recorder 70. On the other hand, depending on which signal is used as the divisor and which is the dividend, the divider module 62 can provide an increasing quotient signal.

The stripchart recorder 70 plots the output of the divider module 62 on the y input vs time. It can be any single channel recorder with enough sensitivity to accept the DC output of the divider module 62 and with an external variable chart speed adjustment to allow for the best resolution of the plot.

The present state of the art has a frequency multiplier 80 available for incorporation into the stripchart recorder for making adjustments in the chart speed via the stepper motor driver for better resolution.

The dashed lines on FIG. 3 show and alternative arrangement to the turbine flowmeter 56 and the linearizer 58. In the alternative arrangement a pulse generator 82 is a shaft encoder driven off of the pulley of pump 52.

There has therefore been described a system in which a single signal can be shown on a stripchart recorder or any suitable meter and a change from a constant signal is indicative of a yield in the flask. In previous systems using stripchart recorders it was essential to have a viewer determine a departure from a constant rate of change on the chart to signify a yield in the flask. In addition, the recorder needed separate inputs for both the pressure and volume signals.

It will be understood that various changes in the details, materials, steps and arrangement of parts, which have been herein described and illustrated in order to explain the nature of the invention, may be made by those skilled in the art within the principle and scope of the invention as expressed in the appended claims.

What is claim is:

1. A dynamic pressure test unit comprising:
a water supply pump for supplying water;
a flask connected to said water supply pump for receiving said water;
a turbine flowmeter connected for measuring the amount of water flow to said flask and for supplying frequency pulses directly proportional to the volume flow rate from said pump to said flask;
linearizer means connected to said flowmeter for minimizing the effects of magnetic drag and increasing the range and linearity of said flowmeter, said linearizer means for providing pulse output signals whose frequency is proportional to the volume flow rate from said pump to said flask;
a frequency to DC transmitter connected to receive the pulse output signals from said linearizer means and providing an output DC signal proportional to the frequency of the received pulse signals;
a variable gain amplifier connected to receive said frequency to DC transmitter DC output for adjusting the gain of said DC output and providing output signals;
a pressure transducer connected for measuring the pressure of water in the flask and for supplying an output of continuous electrical signals indicative of said pressure of water;
a divider network connected to receive said variable gain amplifier output signals and said pressure transducer output signals and providing an output electrical signal indicative of a quotient of the received signals; and
a stripchart recorder connected to receive said output electrical signal from said divider network for displaying said received signal as it varies over a time frame.

* * * * *